US010201673B2

(12) United States Patent
Leppard

(10) Patent No.: US 10,201,673 B2
(45) Date of Patent: Feb. 12, 2019

(54) NEBULIZER, A CONTROL UNIT FOR CONTROLLING THE SAME AND A METHOD OF OPERATING A NEBULIZER

(71) Applicant: KONINKLIJKE PHILIPS N.V., Eindhoven (NL)

(72) Inventor: Michael James Robbert Leppard, Hunston (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 484 days.

(21) Appl. No.: 14/357,590

(22) PCT Filed: Nov. 15, 2012

(86) PCT No.: PCT/IB2012/056431
§ 371 (c)(1),
(2) Date: May 13, 2014

(87) PCT Pub. No.: WO2013/072863
PCT Pub. Date: May 23, 2013

(65) Prior Publication Data
US 2014/0338661 A1 Nov. 20, 2014

Related U.S. Application Data

(60) Provisional application No. 61/559,844, filed on Nov. 15, 2011.

(51) Int. Cl.
A61M 15/00 (2006.01)
A61M 11/00 (2006.01)
(Continued)

(52) U.S. Cl.
CPC ...... A61M 15/0065 (2013.01); A61M 11/005 (2013.01); A61M 15/0085 (2013.01);
(Continued)

(58) Field of Classification Search
CPC ...... A61M 2016/0018; A61M 15/0065; A61M 15/0085; A61M 11/005; A61M 2205/52;
(Continued)

(56) References Cited

U.S. PATENT DOCUMENTS 4,319,155 A    3/1982  Nakai et al.
4,689,515 A *  8/1987  Benndorf ............ B05B 17/0623
                                                           239/102.2

(Continued)

FOREIGN PATENT DOCUMENTS

CN    101489612 A    7/2009
GB    2479953        11/2011
(Continued)

Primary Examiner — Gregory Anderson
Assistant Examiner — Margaret Luarca
(74) Attorney, Agent, or Firm — Michael W. Haas

(57) ABSTRACT

There is provided a method of operating a nebulizer, the method comprising controlling an actuator in the nebulizer to operate in a pulsed operation mode; measuring the sound produced by the nebulizer during operation; and using the measurement of the sound as an indication of the performance of the nebulizer. A control unit for a nebulizer that is configured to perform this method is also described.

14 Claims, 5 Drawing Sheets

Figure 1:
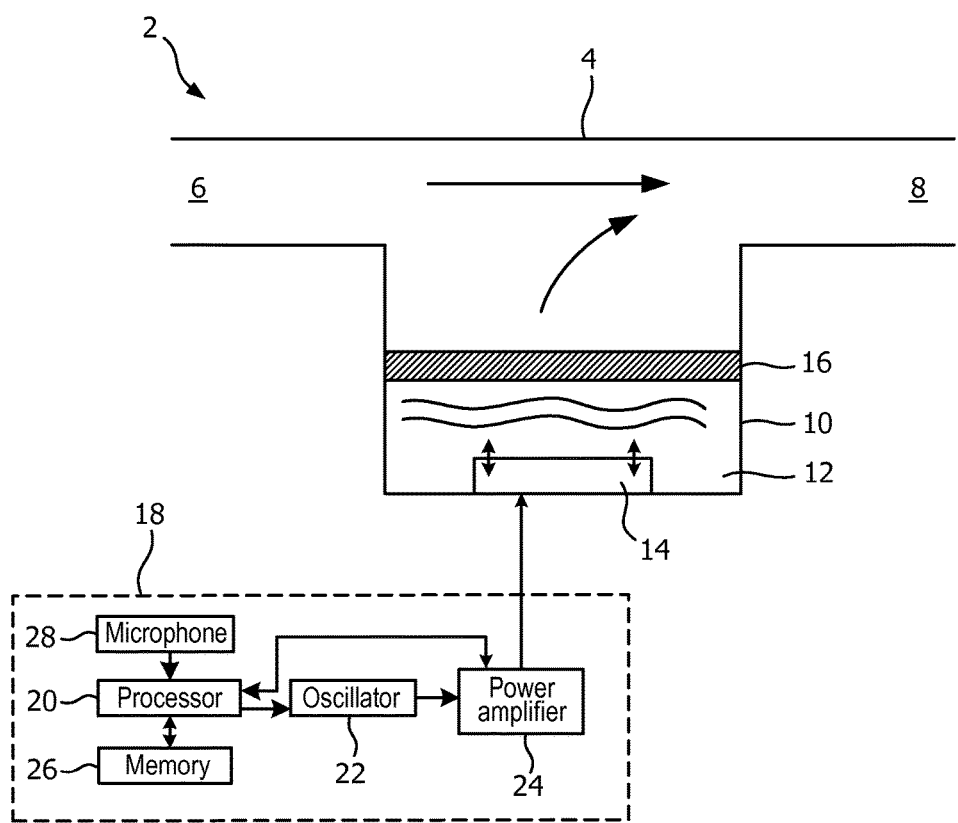
Figure 2:
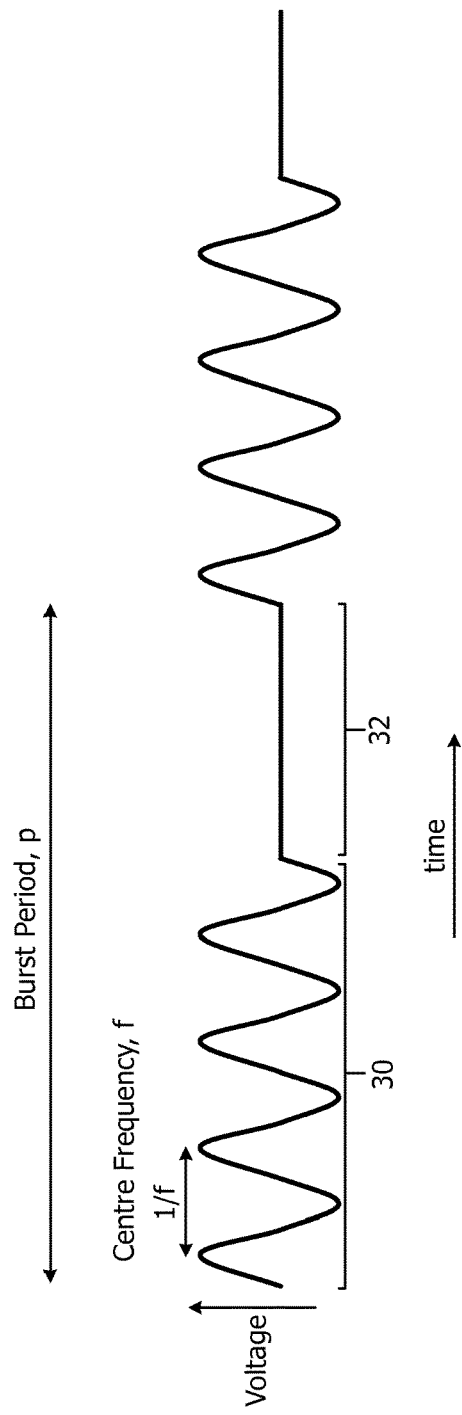

(51) Int. Cl.
*B05B 12/08* (2006.01)
*B05B 17/00* (2006.01)
*B05B 1/00* (2006.01)

(52) U.S. Cl.
CPC ............... *B05B 1/00* (2013.01); *B05B 12/08* (2013.01); *B05B 17/0638* (2013.01); *A61M 2205/3375* (2013.01); *A61M 2205/52* (2013.01)

(58) Field of Classification Search
CPC ...... A61M 2205/3375; A61M 15/0003; A61M 15/0045; A61M 15/0048; A61M 15/0066; A61M 15/0068; A61M 15/008; B05B 17/0638; B05B 17/0623; B05B 12/085; G01F 1/007; G01F 1/00; G01F 22/00; G01F 23/14; G01H 3/00; G10K 9/04
USPC ............ 128/200.14, 200.16, 203.12, 203.14, 128/205.23
See application file for complete search history.

(56) References Cited

U.S. PATENT DOCUMENTS

| | | | |
|---|---|---|---|
| 5,872,727 A * | 2/1999 | Kuo | .................. G10H 1/125 |
| | | | 381/61 |
| 6,152,130 A | 11/2000 | Abrams et al. | |
| 6,679,436 B1 | 1/2004 | Onishi | |
| 7,305,984 B2 | 12/2007 | Altobelli et al. | |
| 2005/0183725 A1 | 8/2005 | Gumaste et al. | |
| 2007/0017506 A1 | 1/2007 | Bell et al. | |
| 2007/0240712 A1 | 10/2007 | Fleming et al. | |
| 2011/0226235 A1* | 9/2011 | Morrison | .......... A61M 15/0085 |
| | | | 128/200.16 |
| 2012/0017894 A1* | 1/2012 | Cinquin | ............... A61M 11/005 |
| | | | 128/200.16 |

FOREIGN PATENT DOCUMENTS

| | | |
|---|---|---|
| JP | 2000160647 A | 6/2000 |
| JP | 2000176014 A | 6/2000 |
| WO | WO199964095 | 12/1999 |
| WO | WO2002078424 | 10/2002 |
| WO | WO2011056889 | 5/2011 |

* cited by examiner

NEBULIZER, A CONTROL UNIT FOR CONTROLLING THE SAME AND A METHOD OF OPERATING A NEBULIZER

CROSS-REFERENCE TO PRIOR APPLICATIONS

This application is the U.S. National Phase application under 35 U.S.C. § 371 of International application Ser. No. PCT/IB2012/056431, filed on NOV. 15, 2012, which claims the benefit of U. S. application Ser. No. 61/559,844, filed on NOV. 15, 2011. These applications are hereby incorporated by reference herein.

TECHNICAL FIELD OF THE INVENTION

The invention relates to a nebulizer that nebulizes a liquid stored therein into fine droplets, for example for inhalation by a user, and in particular relates to a method of operating a nebulizer and a control unit for a nebulizer configured to implement the method.

BACKGROUND TO THE INVENTION

Nebulizers, or atomizers as they are sometimes called, are devices that generate a fine spray or aerosol from a liquid. A particularly useful application for nebulizers is to provide a fine spray containing a dissolved or a suspended particulate drug for administration to a patient by inhalation.

Piezo-mesh based nebulizers are commonly used to generate aerosols in such drug delivery apparatus, whereby for instance a piezoelectric element vibrates a nozzle plate (otherwise referred to as a mesh) to produce the fine aerosol spray. Typically, the holes in the nozzle plate have a diameter of around 2.5 µm and there can be of the order of 5000 nozzles in a typical nozzle plate.

In some nebulizers the piezoelectric element is bonded to a nozzle plate element, whereas in other nebulizers the nozzle plate element is separate from (i.e. not in contact with) the piezoelectric element (sometimes referred to as piezo-cavity-mesh based nebulizers). An advantage of having the nozzle plate element separate from the piezoelectric element is that the nozzle plate element can be removed from the nebulizer and cleaned or entirely replaced after a certain amount of use. These types of nebulizers are also referred to as flat-plate technology (FPT) aerosol generators.

In the conventional nebulizers, liquid to be nebulized is held in a cavity that includes the piezoelectric element and the mesh, which are spaced a small distance apart (for example 1 mm), and the piezoelectric element is continuously vibrated up and down at high frequency so that liquid that is sitting on top of the piezoelectric element is compressed into and through the mesh to form an atomized (nebulized) plume. The driving signal for the piezoelectric element in the conventional nebulizer is typically a sine wave.

As the dosage regime for a particular medicine may need to be precisely controlled, it is necessary to precisely control (or at least know) the output rate of the nebulized liquid so that the correct amount of medication is administered to the user of the nebulizer.

SUMMARY OF THE INVENTION

As described above, when the piezoelectric element and the mesh are spaced by a fixed distance (for example 1 mm) and the piezoelectric element is driven by a continuous sine wave, the nebulizer will nebulize the liquid in the cavity between the mesh and piezoelectric element. These conventional nebulizers make a small amount of noise while operating, but it is white noise (i.e. noise that has no tonal quality).

However, it has been found that if the piezoelectric element is driven with a burst (pulsed) signal (i.e. a sine wave signal that periodically turns on then off), the liquid in the cavity is still nebulized, but the noise that the nebulizer makes while operating is not white noise—it has an audible tone that is related to the burst signal.

It has also been found that the volume of the audible tone can be adjusted by varying the centre frequency of the burst repetition rate, and it has been found that a louder audible tone is associated with a larger plume of nebulized liquid.

Through testing of a particular nebulizer configuration, an optimal set of operating parameters, including the size of the gap between the piezoelectric element and the mesh, centre frequency and the burst repetition rate, can be determined for the nebulizer that provides the highest efficiency in terms of the output rate of the nebulizer and input power required to drive the piezoelectric element.

In addition, during use of piezo-mesh based nebulizers, the mesh can become partially or completely flooded with liquid. For example if the nebulized plume condenses inside the nebulizer, some of the condensed liquid can drop onto the surface of the mesh. When this happens, the output rate of nebulized liquid is reduced as the liquid sitting on top of the mesh blocks the holes, and this leads to a change in the volume of the audible tone produced by the nebulizer. Consequently, it has been found that there is a link between the amplitude of the audible tone produced by the nebulizer and the output rate of the nebulizer.

Thus, according to a first aspect of the invention, there is provided a method of operating a nebulizer, the method comprising controlling an actuator in the nebulizer to operate in a pulsed operation mode; measuring the sound produced by the nebulizer during operation; and using the measurement of the sound as an indication of the performance of the nebulizer. As indicated above, the pulsed operation mode results in a more efficient operation of the nebulizer and the production of an audible tone by the nebulizer, which can easily be measured and analyzed to provide an indication of the performance of the nebulizer.

The pulsed operation mode preferably comprises controlling the actuator to operate in a pulsed operation mode comprises controlling the actuator to be periodically actuated at a first frequency for a first number of cycles and to be at rest for a second number of cycles.

In a preferred embodiment, the step of using the measurement of the sound as an indication of the performance of the nebulizer comprises using the measurement of the sound as an indication of the output rate of nebulized liquid from the nebulizer. Thus, this embodiment provides a simple way to determine the output rate of the nebulizer during normal operation.

In another preferred embodiment, the step of using the measurement of the sound as an indication of the performance of the nebulizer comprises adjusting one or more operating parameters of the nebulizer until the sound produced by the nebulizer is at a predetermined level. Thus, as the volume of the sound produced by the nebulizer indicates the output rate of the nebulizer, the operating parameter(s) can be adjusted until a predetermined sound level (and therefore output rate) is achieved.

Preferably, the predetermined level is a maximum sound level. Thus, in this embodiment the operating parameter(s) are adjusted so that the output rate of the nebulizer is maximized.

Alternatively, the predetermined level is less than a maximum sound level for the nebulizer. Thus, if it is desired to dispense medication at less than a maximum output rate of the nebulizer (for example due to the requirements of a particular dosage regime), the operating parameters can be adjusted until the nebulizer produces a sound that corresponds to that output rate.

In yet another preferred embodiment, wherein the step of using the measurement of the sound as an indication of the performance of the nebulizer comprises, on detecting a change in the sound produced by the nebulizer during operation of the nebulizer from a first sound level, adjusting one or more operating parameters of the nebulizer until the measured sound is within a predetermined range of the first sound level.

In this way, the operation of the nebulizer can be adjusted to counteract the reduction in output rate of the nebulizer that occurs when the nebulizing element (mesh) becomes partially or completely flooded with liquid. This enables the nebulizer to maintain a generally constant output rate of medication to a user, and thus improves the control of the amount of medication dispensed to the user during a particular inhalation.

In some embodiments, the one or more operating parameters is selected from: the first frequency, the period of the pulsed operation mode, a first number of cycles at which the actuator is actuated during the pulsed operation mode, a second number of cycles at which the actuator is at rest during the pulsed operation mode, the amplitude of the control signal used to drive the operation of the actuator, and the distance between the actuator and a nebulizing element arranged to nebulize the liquid upon operation of the actuator.

According to a second aspect of the invention, there is provided a computer program product comprising computer readable code embodied therein, the computer readable code being configured such that, upon execution by a suitable computer or processor, the computer or processor is configured to operate a nebulizer according to the method as described above.

According to a third aspect of the invention, there is provided a control unit for controlling the operation of a nebulizer, the control unit being configured to output a control signal to the actuator to cause the actuator to operate in a pulsed operation mode; receive measurements of the sound produced by the nebulizer during operation; and use the received measurement of the sound as an indication of the performance of the nebulizer.

Preferably, the control unit is configured to output a control signal to the actuator to cause the actuator to be periodically actuated at a first frequency for a first number of cycles and at rest for a second number of cycles.

According to a fourth aspect of the invention, there is provided a nebulizer comprising a reservoir chamber for storing liquid to be nebulized, an actuator that is configured to vibrate in order to nebulize the liquid stored in the reservoir chamber; a nebulizing element arranged to nebulize the liquid upon operation of the actuator; a sound detecting device configured to measure the sound produced by the nebulizer during operation; and a control unit configured as described above.

BRIEF DESCRIPTION OF THE DRAWINGS

Exemplary embodiments of the invention will now be described, by way of example only, with reference to the following drawings, in which:

FIG. 1 is a block diagram of a nebulizer according to an embodiment of the invention;

FIG. 2 is a diagram illustrating an exemplary signal for controlling an actuator in a nebulizer according to the invention;

FIG. 3 is a flow chart illustrating a method of operating a nebulizer according to an embodiment of the invention;

FIG. 4 shows two graphs comparing the sound measured during operation of a nebulizer to the power consumed and the output rate; and FIG. 5 is a flow chart illustrating a method of operating a nebulizer according to another embodiment of the invention.

DETAILED DESCRIPTION OF THE PREFERRED EMBODIMENTS

FIG. 1 shows an exemplary nebulizer 2. The nebulizer 2 comprises a body 4 having an inlet 6 and an outlet 8 arranged so that when a user of the nebulizer 2 inhales through the outlet 8, air is drawn into and through the nebulizer 2 via the inlet 6 and outlet 8 and into the user's body. The outlet 8 is typically provided in the form of a mouthpiece or a facial or nasal mask or in a form that is suitable for connection to a separate replaceable mouthpiece or facial or nasal mask.

The nebulizer 2 comprises a reservoir chamber 10 between the inlet 6 and outlet 8 for storing a liquid 12, for example a medication or drug, to be nebulized (i.e. to be turned into a fine mist or spray). The nebulizer 2 is configured such that fine droplets of the nebulized liquid 12 combine with the air drawn through the nebulizer 2 when the user inhales to deliver a dose of the medication or drug to the user.

An actuator 14 is provided for agitating or vibrating the liquid 12 stored in the reservoir chamber 10. In the embodiments of the invention that are described further below, the actuator 14 is provided in the form of a piezoelectric element. However, those skilled in the art of nebulizers will appreciate that other forms of actuator 14 can be used in nebulizers according to the invention. It will also be appreciated that a piezoelectric element 14 can be covered with a plastic or metal cover layer to avoid direct contact between the piezoelectric element and the liquid 12.

A nebulizing element 16 in the form of a nozzle plate is provided in the reservoir chamber 10 for nebulizing the liquid 12 when the liquid 12 is vibrated by the actuator 14. The nozzle plate 16 is typically in the form of a mesh or membrane having a plurality of small holes or nozzles through which small amounts of the liquid can pass. The size (diameter) of the nozzles in the nozzle plate 16 determines, among other things, the size of the droplets of liquid produced when the nebulizer 2 is activated. The size of the droplets of liquid produced can be measured in terms of the mass mean diameter (MMD). The nozzle plate 16 can be removable from the nebulizer 2 so that it can be cleaned or completely replaced, as required.

In the illustrated embodiment, the actuator 14 is separate from the nozzle plate 16 and is positioned at, or proximate to, the bottom of the reservoir chamber 10 in order to agitate the liquid 12. However, in alternative embodiments the actuator 14 can be in contact with or integral with the nozzle plate 16 and can vibrate the nozzle plate 16 in order to nebulize the liquid 12.

In use, the liquid 12 fills the reservoir chamber 10 up to the height of the nozzle plate 16. It will be appreciated that the liquid 12 in the reservoir chamber 10 will be depleted as the nebulizer 2 is operated, and more liquid 12 must be added to the reservoir chamber 10 to maintain the liquid 12 at the required height for the nebulizer 2 to continue operating. Therefore, the nebulizer 2 may comprise, or be coupled to, a further chamber (not shown in FIG. 1) that stores liquid for replenishing the liquid 12 in the reservoir chamber 10. The liquid from the further chamber may flow into the reservoir chamber 10 due to the action of gravity and/or capillary filling.

The nebulizer 2 further comprises a control unit 18 that controls the operation of the nebulizer 2. The control unit 18 comprises a processor 20 that generally controls the operation of the nebulizer 2. The control unit 18 also comprises a variable-frequency oscillator 22 that generates a generally sinusoidal signal and that is connected to the processor 20 and a power amplifier 24. The power amplifier 24 amplifies the signal from the oscillator 22 and outputs the signal that is used to drive the actuator 14. The power amplifier 24 also provides an indication of the power used by the power amplifier 24 to the processor 20. The processor 20 controls the oscillator 22 (and also optionally the power amplifier 24) to generate the control signals for the actuator 14 that cause the actuator 14 to operate (vibrate) and nebulize the liquid 12 as described further below.

A memory 26 is also provided in the control unit 18 that can store nebulizer operating parameters, medicament information and/or program instructions for use by the processor 20 during operation of the nebulizer 2. The medicament information may, for example, relate to the dosage regime to be provided by the nebulizer 2, such as the required treatment time and/or medication flow rate.

In accordance with the invention, the control signals output to the actuator 14 by the power amplifier 24 (under the control of the processor 20 and oscillator 22) cause the actuator 14 to operate in a 'pulsed' operation mode. In the pulsed operation mode, the control signal causes the actuator 14 to actuate (vibrate) at a frequency f for a particular number of consecutive cycles, and then causes the actuator 14 to rest (i.e. not vibrate) for a further number of consecutive cycles. This actuated and non-actuated operation is repeated periodically during the operation of the nebulizer 2. The period of this pulsed operation mode (i.e. the total period of the actuated and non-actuated portions) is termed the 'burst repetition rate'.

An exemplary control signal for this 'pulsed' operation shown in FIG. 2 where it can be seen that the control signal comprises an active portion 30 (also referred to herein as the 'pulse') comprising four cycles of actuation at frequency f, followed by a rest portion 32 in which the actuator 14 is not actuated and is at rest. The combined length of the active portion 30, referred to as the 'pulse length', or 'number of cycles' herein (and which can be defined as the number of cycles of the signal at frequency f that are in the active portion 30), and the non-actuated (rest) portion 32 is the burst period, p (i.e. the burst repetition rate). It will be appreciated that although four cycles of actuation are shown in this exemplary signal, in practice the active portion 30 will comprise substantially more than four cycles.

Put another way, the control signal output to the actuator 14 by the power amplifier 24 can be said to comprise a time-varying/sinusoidal portion (active portion 30) with frequency f that causes the actuator 14 to actuate (vibrate) at that frequency f, followed by a time-invariant portion (inactive portion 32) in which the actuator 14 is in an inactive state.

The active portion 30 can be generated by the processor 20 controlling the oscillator 22 to output a sinusoidal signal for the required pulse length/number of cycles, and the inactive portion 32 can be generated by the processor 20 controlling the oscillator 22 to output a signal with constant voltage for the required duration/number of cycles.

In one particular implementation of the invention, the centre frequency f of the signal in the active portion 30 is at or around 1 MHz (so the oscillator 22 generates a signal having a frequency of 1 MHz), the burst repetition rate is 1 ms (so corresponding to a burst period p of 1 ms—i.e. 1000 cycles of the 1 MHz signal) and a duty cycle of 20% (i.e. the length of the active portion 30 is 0.2 ms or 200 cycles of the 1 MHz signal). It will be appreciated that in other implementations the frequency f, burst repetition rate and/or duty cycle can take other values.

As indicated above, it has been found that if the nebulizing element 16 is driven with this burst (pulsed) signal, the liquid in the reservoir chamber 10 is nebulized and the nebulizer 2 produces an audible tone that is related to the burst repetition rate. As also indicated above, it has been found that there is a link between the characteristics of the audible tone produced by the nebulizer 2 and the performance of the nebulizer 2, and thus the audible tone can be used as a measure of the performance (for example the output rate) of the nebulizer 2.

Therefore, the nebulizer 2 is provided with a microphone 28 that is used to measure the sound produced by the nebulizer 2 during operation. The microphone 28 provides the measurements to the processor 20 for processing. In the illustrated embodiment, the microphone 28 is located in the control unit 18, although it will be appreciated that the microphone 28 could be located elsewhere in the nebulizer 2, for example in the body 4 of the nebulizer 2.

In an alternative embodiment, it will be appreciated that the nebulizer 2 can be provided with an alternative type of sound detecting device to the microphone 28, such as a vibration sensor (for example a MEMS-type vibration sensor).

In order to be able to use the signal from the microphone 28 to measure the output rate of the nebulizer 2, the signal from the microphone 28 is processed in the processor 20 in order to extract the audible tone associated with the operation of the nebulizer 2. In particular, the signal from the microphone 28 is amplified and filtered, preferably by a band pass filter, and more preferably by a high Q band pass filter. This filter effectively removes any external sounds in the microphone signal, including any sound generated by the inhalation of the user of the nebulizer 2, and just passes a frequency band generally centered around the burst frequency (which is 1/burst repetition rate). Thus, in the example above where the burst rate is 1 ms, the band pass filter will pass frequencies in a band centered around 1 kHz. The processor 20 can then measure characteristics of the filtered signal, for example the volume or level of the sound (as represented by the amplitude of the signal).

As indicated above, it has been found that varying the operating parameters of the nebulizer 2 has an effect on the sound produced by the nebulizer 2, and by analyzing the sound produced by the nebulizer 2, an optimal set of operating parameters can be determined. The operating parameters that can be varied in a particular nebulizer 2 can relate to the control signal provided to the actuator 14, and/or to other aspects of the nebulizer 2. The 'optimal' operating parameters can be those operating parameters that cause the nebulizer 2 to operate in the most efficient way (for example by maximizing the ratio of output rate to input power) or to operate with the highest possible output rate. Alternatively, the 'optimal' operating parameters can be those operating parameters that cause the nebulizer 2 to operate at a predetermined output rate (where that output rate is less than the maximum possible output rate, but nonetheless desirable for dispensing a particular medication).

The operating parameters relating to the control signal that can be varied include, but are not limited to, the frequency of oscillation of the oscillator 22, the burst repetition rate (i.e. the burst period p of the control signal), the amplitude (peak voltage) of the control signal (where the amplitude/voltage of the control signal determines the degree of actuation of the actuator 14), the duty cycle (i.e. the proportion of the control signal in which the actuator 14 is driven), the length of the active portion 30, and/or the length of the rest portion 32.

An operating parameter relating to the nebulizer 2 that can be varied is the distance between the nozzle plate 16 and the actuator 14.

Figure 3:
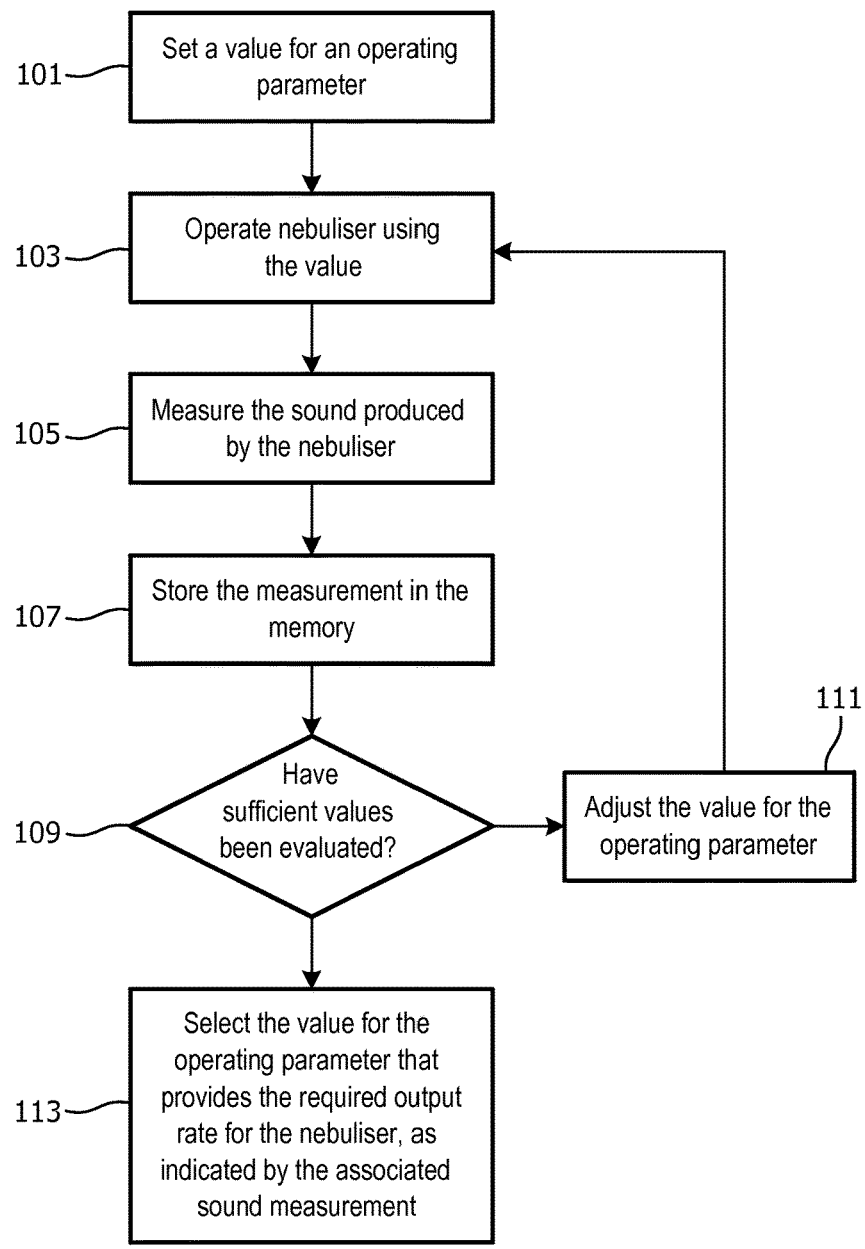

The flow chart in FIG. 3 illustrates a method of determining a value for an operating parameter that provides a required output rate of nebulized liquid. This method can be performed during a calibration procedure before the nebulizer 2 is used to dispense medication to a user, or alternatively the method can be performed to adjust the output rate while the nebulizer 2 is dispensing medication to the user.

In step 101, an initial value for the operating parameter of the nebulizer 2 to be optimized is set. In one particular example, the operating parameter to be optimized is the frequency f of the control signal, and the initial value is set as 1 MHz. Other operating parameters (which are not optimized in this procedure), including the burst repetition rate and duty cycle, are set at 1 ms and 20% respectively.

The nebulizer 2 is then operated using the initial value for the operating parameter (step 103), and the sound produced by the nebulizer 2 is measured using the microphone 28 (step 105).

The signal from the microphone 28 can be processed as described above to effectively remove any external sounds from the signal, and the volume (amplitude) of the sound remaining in the signal determined. The determined volume is then stored in the memory 26 (step 107). Other information on the operation of the nebulizer 2 can also be stored in the memory 26. For example, the power supplied by the power amplifier 24 when the operating parameter using the initial value can also be stored in the memory 26.

In step 109, it is determined whether a sufficient number of values for the operating parameter have been evaluated in order to determine the optimal operating parameter value. The required number of values to be evaluated will depend on the operating parameter being evaluated, the total range of values that need to be evaluated and the resolution at which the nebulizer 2 can vary that parameter.

If a sufficient number of values have not yet been assessed, the method passes to step 111 in which the initial value for the operating parameter is adjusted to a new value and then steps 103 to 109 are repeated for the new value.

In the example where the operating parameter to be optimized is the frequency f of the control signal, the nebulizer 2 can be configured to assess frequency values in the range 1 MHz±50 kHz with a resolution of 1 kHz.

Once a sufficient number of values have been evaluated, the method passes to step 113 in which the 'optimal' value for the operating parameter that provides the required output rate for the nebulizer 2 is determined.

Figure 4:
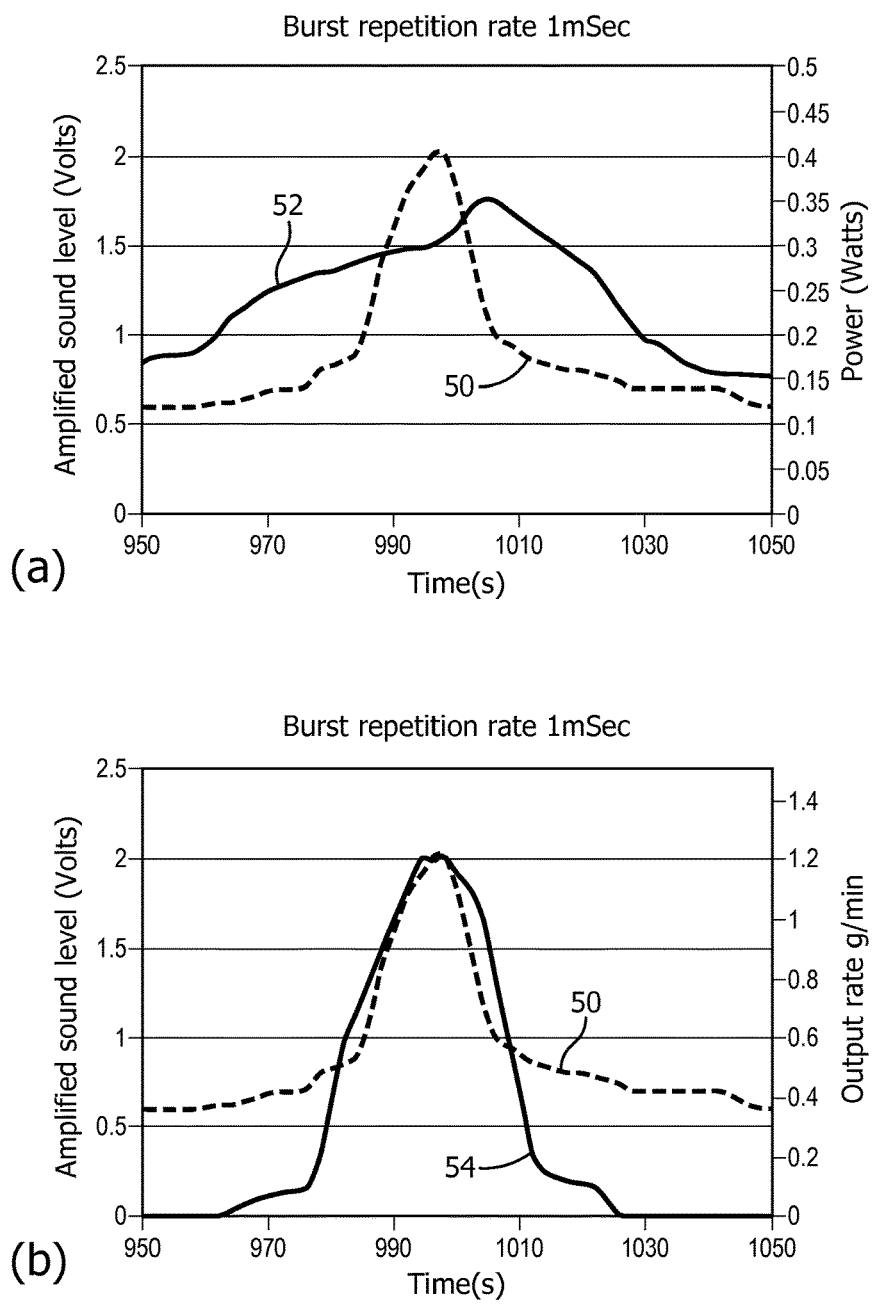

The graph shown in FIG. 4(*a*) shows the results of the above method for the frequency example, and shows the variation in volume (amplitude) of the measured sound across the frequency range 950 kHz to 1050 kHz (represented by line 50) and the corresponding variation power supplied by the power amplifier 24 (represented by line 52).

Thus, it can be seen that the power supplied peaks at 1006 kHz, which corresponds to the resonant frequency of the actuator 14 (piezoelectric element), but the volume of the sound produced by the nebulizer 2 peaks at 998 kHz, which has been found to correspond to the resonant frequency of the complete nebulizer 2 (i.e. the actuator 14, nebulizing element 16 and reservoir chamber 10). Thus, the optimal value for the frequency The graph in FIG. 4(*b*) shows the same sound measurement results plotted against measurements of the output rate (measured in grams/minute and indicated by line 54) of the nebulizer 2 taken over the same frequency range. Thus, it can be seen that the amplitude and output rate peak at almost exactly the same frequency (998 kHz), and the relationship between the amplitude and output rate is generally linear within around 10 kHz of the burst frequency (1 MHz).

Therefore, if it is desired to operate the nebulizer 2 at the highest possible output rate, the optimal operating frequency f is 998 kHz.

As described above, during use a nebulizer 2, the nebulizing element 16 can become partially or completely flooded with liquid if the nebulized plume condenses inside the nebulizer 2 and some of the condensed liquid drops onto the surface of the element 16. When this happens, the output rate of nebulized liquid is reduced as the liquid sitting on top of the nebulizing element 16 blocks the holes. The output rate of the nebulizer 2 can also be affected by the height of the liquid in the reservoir chamber 10 (and therefore the pressure on the nebulizing element 16), any heating of the nebulizer 2 that occurs during operation and the formation of bubbles on the on the liquid side of the nebulizing element 16.

Figure 5:
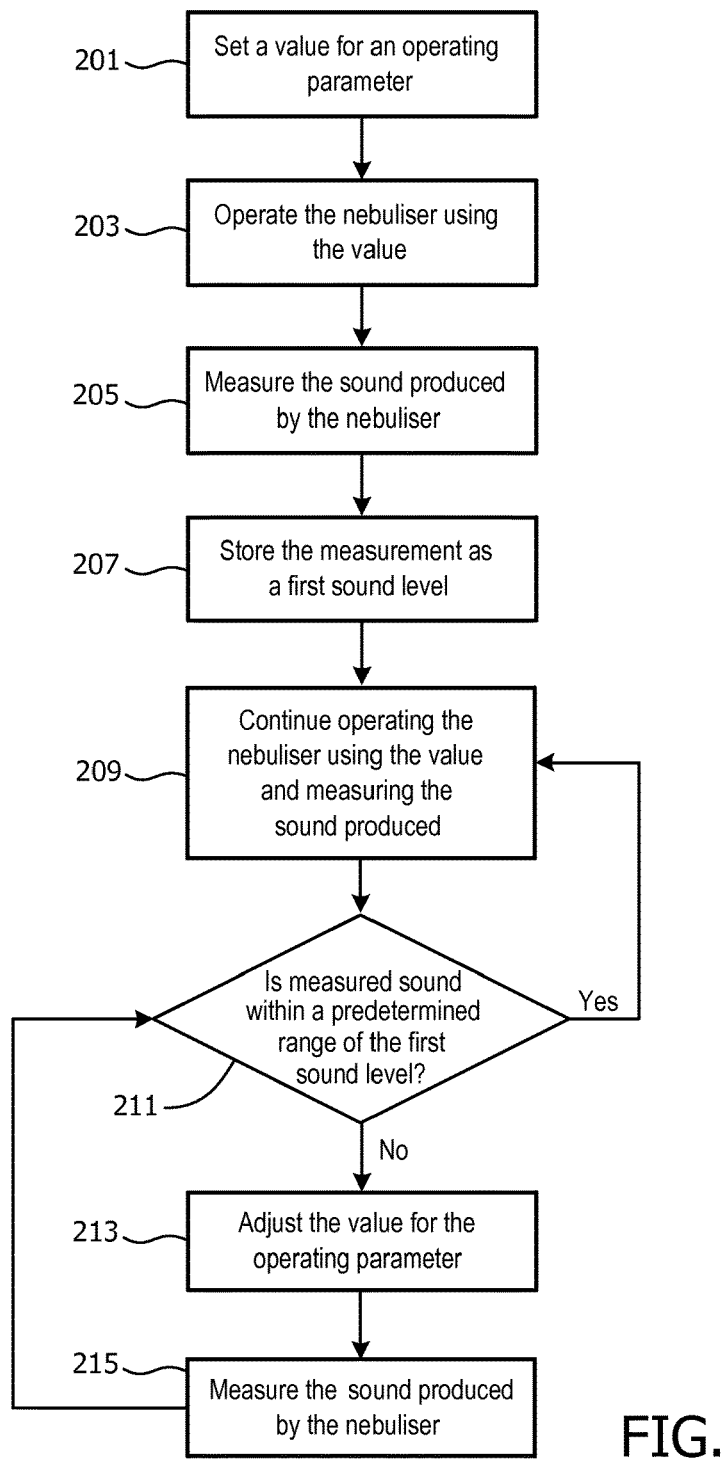

Therefore, an embodiment of the invention provides a way of overcoming these problems, and an exemplary method is shown in FIG. 5. Briefly, the processor 20 monitors the sound produced by the nebulizer 2 during operation, and if the sound varies from an initial value (indicating that there has been a change in the output rate), the processor 20 can adjust the (or an) operating parameters of the nebulizer 2 in order to restore or maintain the sound at the initial value (and therefore restore or maintain the required output rate).

In FIG. 5, steps 201, 203, 205 and 207 generally correspond to steps 101, 103, 105 and 107 in FIG. 3 respectively, with the main difference being that steps 201, 203, 205 and 207 are typically only performed during use of the nebulizer 2 rather than during a calibration or initialization procedure.

The value set for the operating parameter in step 201 can be the 'optimal' value determined using the method in FIG. 3, and thus, continuing the example described above, the frequency f of the oscillator 22 can be set to 998 kHz. In step 207, the sound level (volume) measured for the operating frequency of 998 kHz is stored as a first sound level value.

Operation of the nebulizer 2 using the set frequency continues and the sounds produced by the nebulizer 2 are periodically measured (step 209).

In step 211, the last sound measurement is compared to the first sound level value. If the last sound measurement is within a predetermined range of the first sound level, then the method returns to step 209. The predetermined range can be set based on the geometries of the actuator 14, reservoir chamber 10 and oscillator frequency.

However, if the last sound measurement differs from the first sound level value by more than the predetermined amount or falls outside the predetermined range, then the processor 20 can adjust the value for an operating parameter in order to try and restore the sound level produced by the nebulizer 2 to the first sound level (step 213). In one exemplary embodiment, the processor 20 can adjust the power supplied by the power amplifier 24 (and thus the amplitude of the control signal) in order to increase the volume of the sound produced by the nebulizer 2. However, it will be appreciated that the processor 20 can adjust other operating parameters of the nebulizer 2 to change the volume of the sound.

Following this adjustment, the sound produced by the nebulizer 2 is again measured (step 215), and the method returns to step 211 to compare this measurement to the first sound level value. Steps 211, 213 and 215 can be repeated throughout the operation of the nebulizer 2 in order to maintain the output rate at the desired level.

It will be appreciated that, in addition to the control unit 18 and methods described above, the invention can be provided in the form of a computer program carried on a computer readable medium that is configured to cause the processor 20 in the control unit 18 to execute the steps shown in FIGS. 3 or 5. This program could be stored in memory 26.

Those skilled in the art will appreciate that the word "nebulizer" can be used interchangeably with the term drug delivery apparatus or atomizer, and the use of the word "nebulizer" is intended to cover forms and designs of nebulizer other than the specific type of nebulizer described above and illustrated in the Figures.

Furthermore, although the invention has been described in terms of a nebulizer that is primarily for use in administering a medicament, it will be appreciated that the invention can be applied to any other type of nebulizer or device in which a nebulizing element (nozzle plate) is actuated in order to nebulize a liquid, such as, for example an air humidifier, an electric shaver, a steam iron or a perfume dispenser.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of operating a nebulizer, the method comprising:

outputting a control signal to an actuator in the nebulizer to control the actuator to operate in a pulsed operation mode, wherein the control signal causes the actuator to periodically actuate at a first frequency for a first number of cycles of the first frequency during an active portion and to be at rest for a second number of cycles of the first frequency during a rest portion, the pulsed operation mode having a period equal to a combined length of the active portion and the rest portion;

measuring a sound produced by the nebulizer when the actuator is operating in the pulsed operation mode;

processing the measurement of the sound to extract an audible tone associated with the operation of the nebulizer, wherein the processing includes providing a filtered signal centered around a frequency corresponding to the inverse of the period of the pulsed operation mode;

using a volume or level of the audible tone as an indication of an output rate of nebulized liquid from the nebulizer;

detecting a change in the volume of the audible tone; and adjusting, in response to detecting the change, distance between the actuator and a nebulizing element until the volume of audible tone is within a predetermined range.

2. The method of operating a nebulizer as claimed in claim 1, further comprising, responsive to the audible tone not reaching a predetermined level, adjusting one or more additional operating parameters of the nebulizer until the audible tone produced by the nebulizer reaches the predetermined level.

3. The method of operating a nebulizer as claimed in claim 2, wherein the predetermined level is a maximum sound level.

4. The method of operating a nebulizer as claimed in claim 2, wherein the predetermined level is less than a maximum sound level.

5. The method of operating a nebulizer as claimed in claim 1, wherein the nebulizing element is configured to nebulize the liquid upon operation of the actuator, and the method further comprising, responsive to detecting the change in the volume of the audible tone produced by the nebulizer during operation of the nebulizer from a first sound level, adjusting the distance until the volume of the audible tone is within the predetermined range of the first sound level.

6. The method of operating a nebulizer as claimed in claim 2, wherein the one or more additional operating parameters comprises one or more of the first frequency, the period of the pulsed operation mode, the first number of cycles at which the actuator is actuated during the pulsed operation mode, the second number of cycles at which the actuator is at rest during the pulsed operation mode, or an amplitude of the control signal used to drive the operation of the actuator.

7. The method of operating a nebulizer as claimed in claim 1, wherein the change in the volume of the audible tone corresponds to the volume of the audible tone being outside the predetermined range.

8. A computer program product comprising computer readable code embodied therein, the computer readable code being configured such that, upon execution by a suitable computer or processor, the computer or processor is configured to operate a nebulizer according to the method comprising:

outputting a control signal to an actuator in the nebulizer to control the actuator to operate in a pulsed operation mode, wherein the control signal causes the actuator to periodically actuate at a first frequency for a first number of cycles of the first frequency during an active portion and to be at rest for a second number of cycles of the first frequency during a rest portion, the pulsed operation mode having a period equal to a combined length of the active portion and the rest portion;

measuring a sound produced by the nebulizer when the actuator is operating in the pulsed operation mode;

processing the measurement of the sound to extract an audible tone associated with the operation of the nebulizer, wherein the processing includes providing a filtered signal centered around a frequency corresponding to the inverse of the period of the pulsed operation mode;

using a volume or level of the audible tone as an indication of an output rate of nebulized liquid from the nebulizer;

detecting a change in the volume of the audible tone; and adjusting, in response to detecting the change, distance between the actuator and a nebulizing element until the volume of audible tone is within a predetermined range.

9. A control unit for controlling operation of a nebulizer, the control unit being configured to:

output a control signal to an actuator in the nebulizer to control the actuator to operate in a pulsed operation mode, wherein the control signal causes the actuator to periodically actuate at a first frequency for a first number of cycles of the first frequency during an active portion and to be at rest for a second number of cycles of the first frequency during a rest portion, the pulsed operation mode having a period equal to a combined length of the active portion and the rest portion;

receive measurements of a sound produced by the nebulizer when the actuator is operating in the pulsed operation mode;

process the received measurement of the sound to extract an audible tone associated with the operation of the nebulizer, wherein the processing includes providing a filtered signal centered around a frequency corresponding to the inverse of the period of the pulsed operation mode;

use a volume or level of the audible tone as an indication of an output rate of nebulized liquid from the nebulizer;

detect a change in the volume of the audible tone; and adjust, in response to detecting the change, distance between the actuator and a nebulizing element until the volume of audible tone is within a predetermined range.

10. The control unit as claimed in claim 9, wherein the control unit is further configured to, responsive to the audible tone not reaching a predetermined level, adjust one or more additional operating parameters of the nebulizer until the audible tone reaches the predetermined level.

11. The control unit as claimed in claim 9, wherein the nebulizing element is configured to nebulize the liquid upon operation of the actuator, and wherein the control unit is further configured to, responsive to detecting the change in the volume of the audible tone produced by the nebulizer during operation of the nebulizer from a first sound level, cause the distance until the volume of the audible tone is within a predetermined range of the first sound level.

12. The control unit as claimed in claim 10, wherein the one or more additonal operating parameters comprises one or more of the first frequency, the period of the pulsed operation mode, the first number of cycles at which the actuator is actuated during the pulsed operation mode, the second number of cycles at which the actuator is at rest during the pulsed operation mode, or an amplitude of the control signal used to drive the operation of the actuator.

13. A nebulizer, comprising:

a reservoir chamber for storing liquid to be nebulized;

an actuator that is configured to vibrate in order to nebulize the liquid stored in the reservoir chamber;

a nebulizing element arranged to nebulize the liquid upon operation of the actuator;

a sound detecting device configured to measure the sound produced by the nebulizer during operation; and a control unit as claimed in claim 9.

14. The control unit as claimed in claim 9, wherein the change in the volume of the audible tone corresponds to the volume of the audible tone being outside the predetermined range.

* * * * *